United States Patent [19]

Astle

[11] Patent Number: 4,562,871
[45] Date of Patent: Jan. 7, 1986

[54] REHYDRATOR

[76] Inventor: Thomas W. Astle, 607 Harborview Rd., Orange, Conn. 06477

[21] Appl. No.: 590,337

[22] Filed: Mar. 16, 1984

[51] Int. Cl.⁴ .................................................. B65B 3/10
[52] U.S. Cl. .................................... 141/129; 141/236; 141/238; 141/256; 141/286; 251/7; 422/103
[58] Field of Search ............................ 251/4–10; 141/129–191, 234–248, 67, 250–286; 422/67, 99, 100, 101, 102, 103

[56] References Cited

U.S. PATENT DOCUMENTS

| | | | |
|---|---|---|---|
| 3,188,181 | 6/1965 | Peterson et al. | 23/259 |
| 3,319,512 | 5/1967 | Isreeli | 88/14 |
| 3,536,449 | 10/1970 | Astle | 23/230 |
| 3,568,735 | 3/1971 | Lancaster | 141/238 |
| 3,650,306 | 3/1972 | Lancaster | 141/238 |
| 3,776,700 | 12/1973 | Galiant | 23/259 |
| 3,832,135 | 8/1974 | Drozdowski et al. | 23/230 |
| 3,854,507 | 12/1974 | Nishioka et al. | 141/130 |
| 4,058,146 | 11/1977 | Citrin | 141/1 |
| 4,115,200 | 9/1978 | Anderson | 195/127 |
| 4,231,989 | 11/1980 | Thoma | 422/63 |
| 4,276,048 | 6/1981 | Leaback | 23/230 |
| 4,294,802 | 10/1981 | Johanssen | 422/103 |
| 4,359,075 | 11/1982 | Eberle et al. | 141/177 |
| 4,422,151 | 12/1983 | Gilson | 141/130 |

Primary Examiner—Houston S. Bell, Jr.
Attorney, Agent, or Firm—Costas, Montgomery & Dorman

[57] ABSTRACT

A rehydrator which dispenses precise amounts of liquid to each row of wells in a titration tray where the dispensing of the liquid is performed through valving means in timed relation to indexing of the platform to present a row of wells beneath the dispensing orifices. The indexing of the tray and the valving means are accomplished by the same drive means to obtain the timed relation.

24 Claims, 8 Drawing Figures

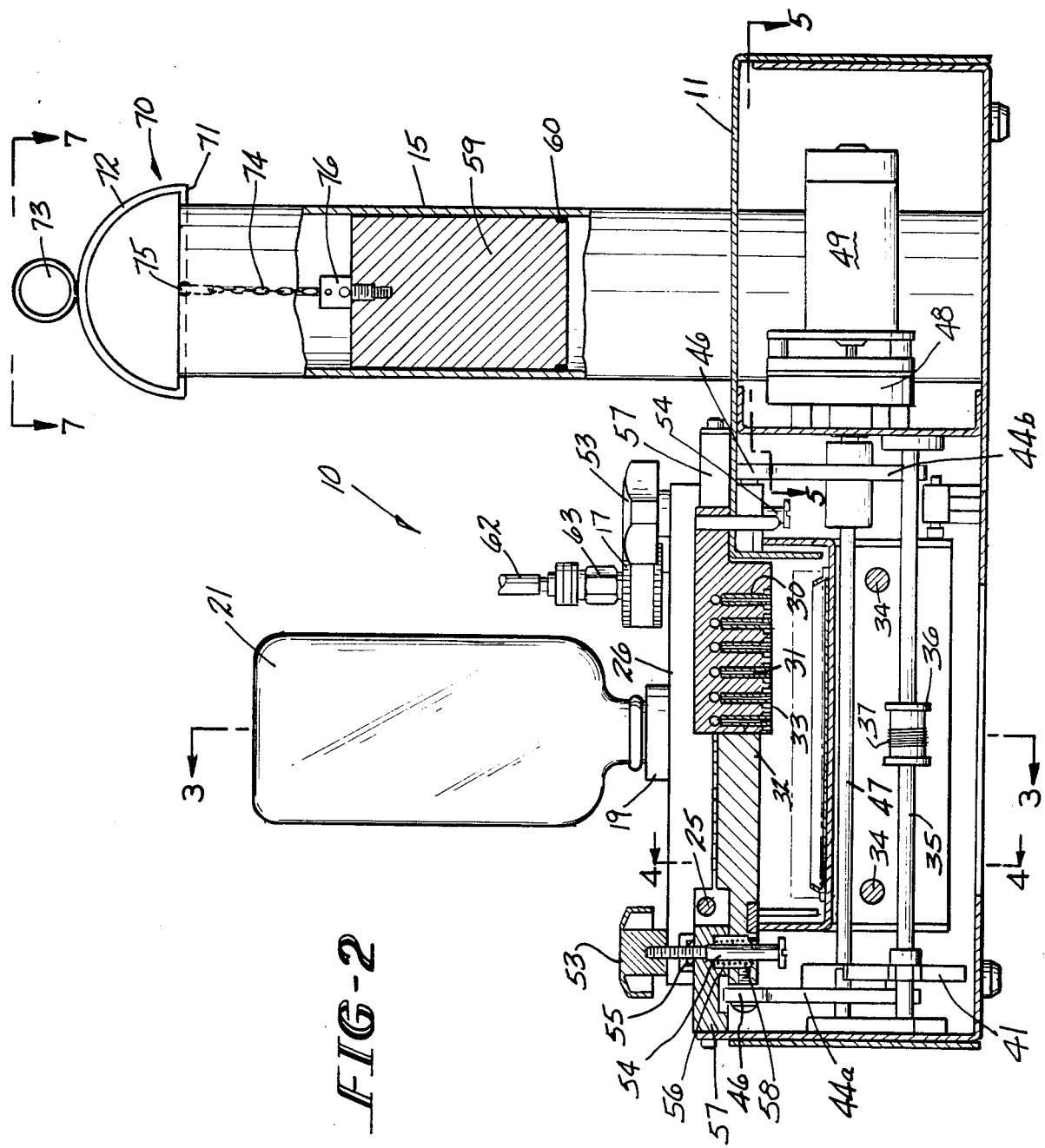

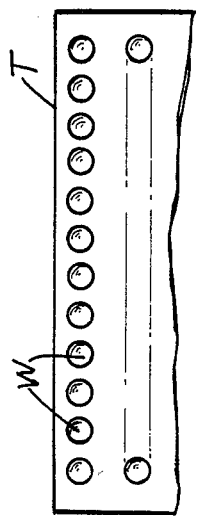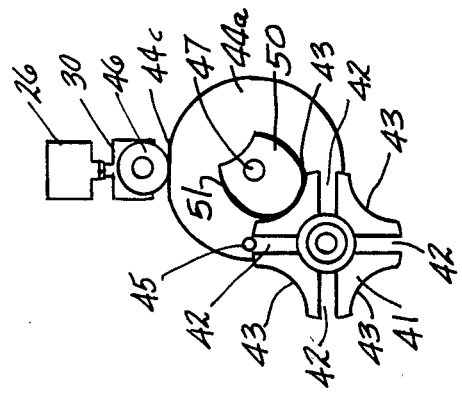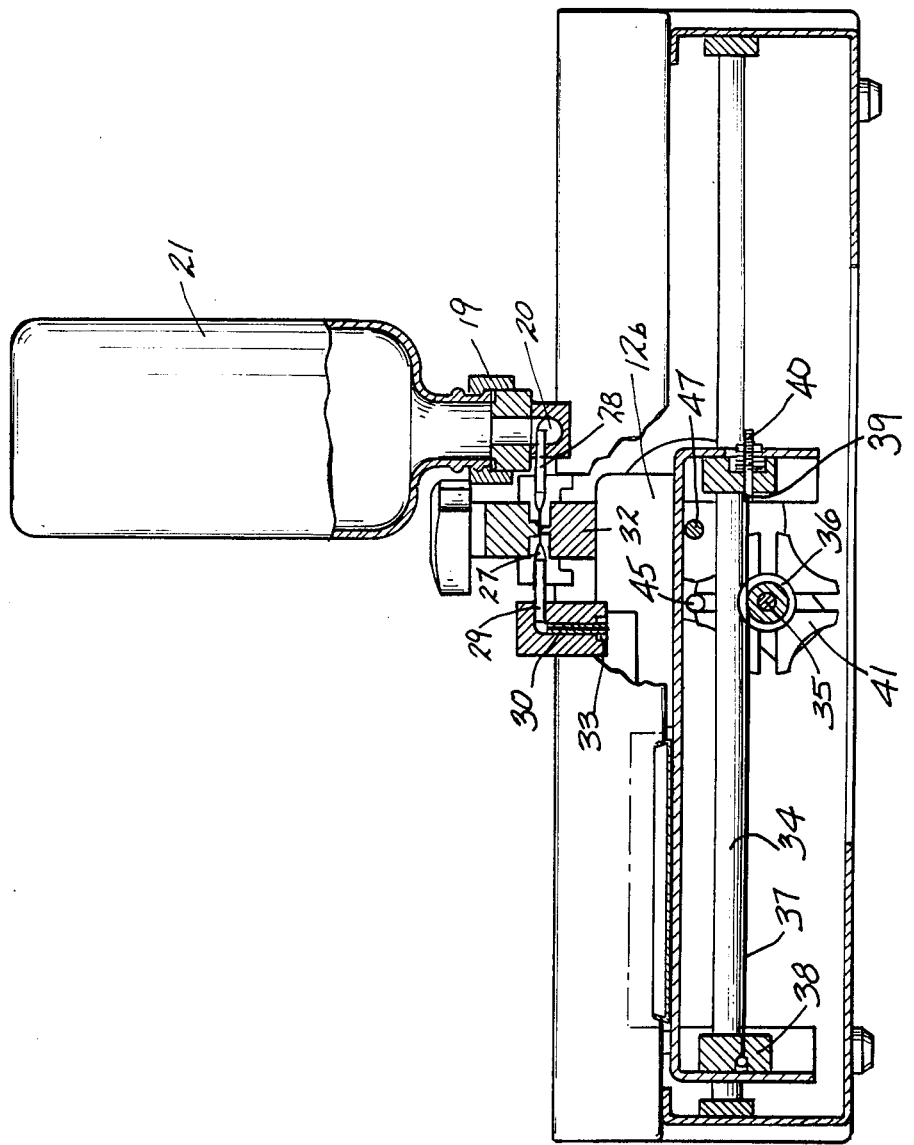

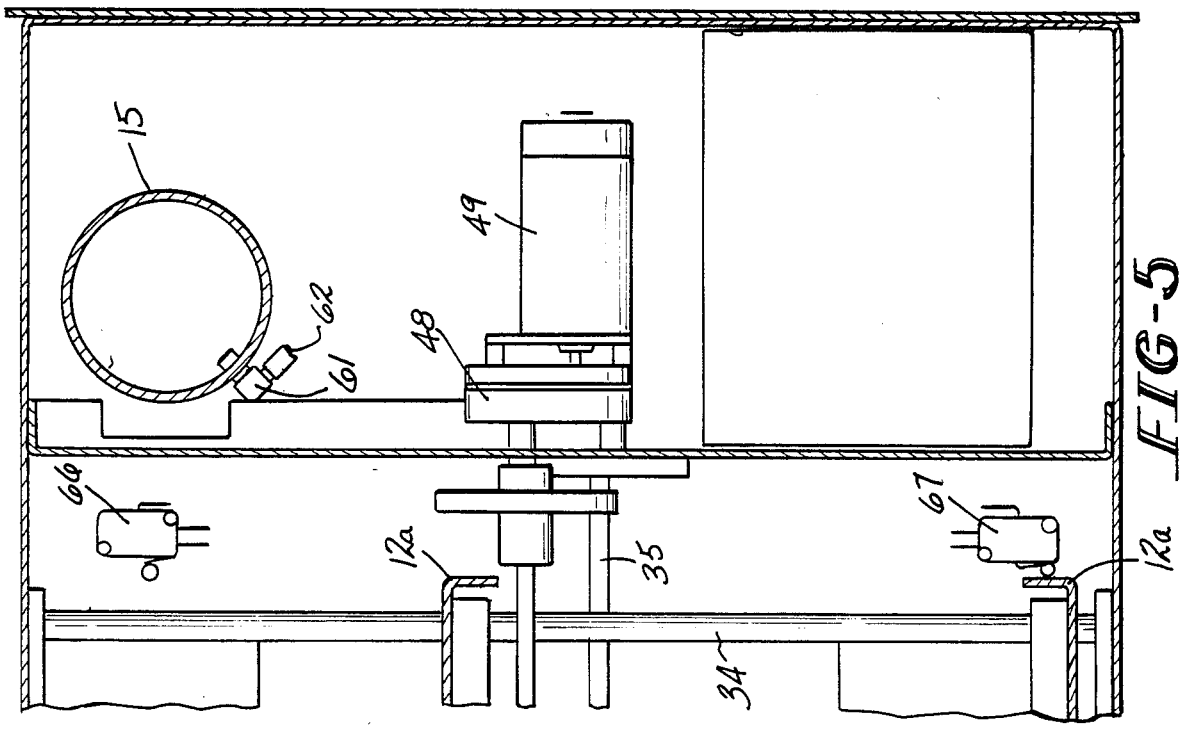
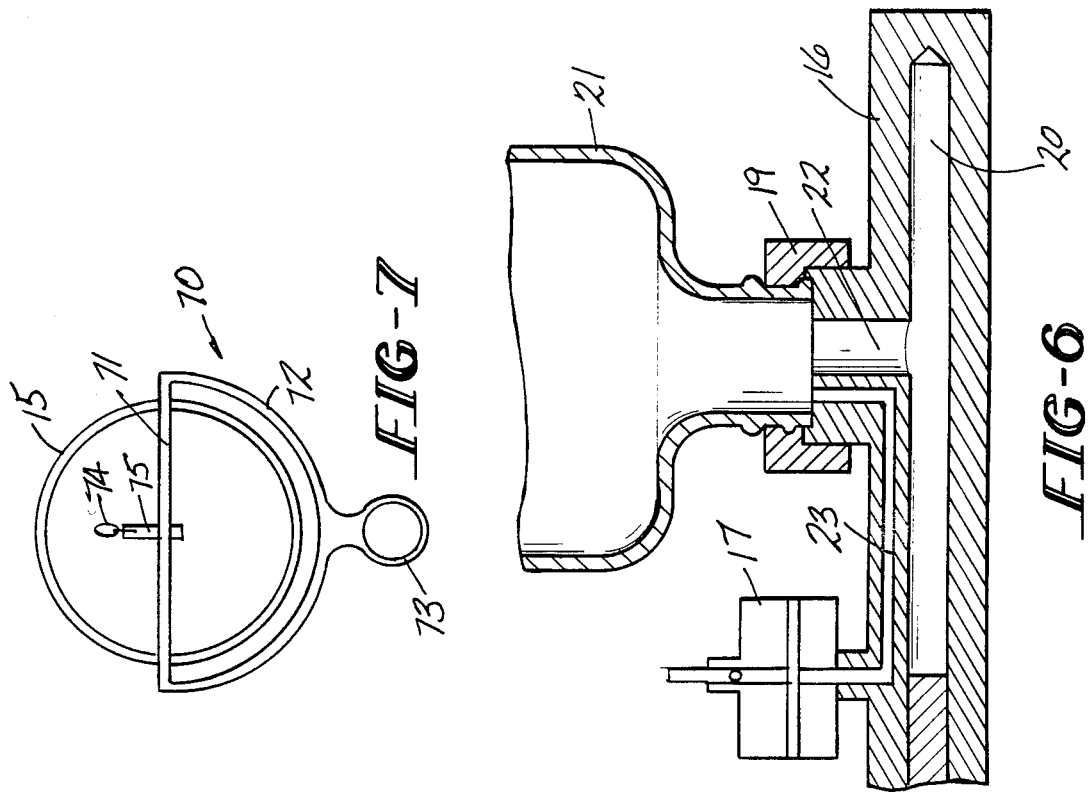

REHYDRATOR

FIELD OF THE INVENTION

This invention relates to an apparatus for adding a precise amount of liquid to a plurality of receptacles and, more particularly, relates to an apparatus for rehydrating dried reagents in a titration tray.

BACKGROUND OF THE INVENTION

In various fields of laboratory work, there is a need to deliver reagents in measured quantities to a plurality of receptacles. A typical example is antimicrobial susceptibility testing in the clinical microbiology laboratory. A test tray may be supplied in a dry form to facilitate shipping and to lengthen its shelf life. The test tray consists of a number of wells, each containing a different antimicrobial concentration or a biochemical for organism identification. Prior to use, the laboratory must rehydrate the tray by adding liquid to each well to resuspend the reagents contained therein.

Another example of adding liquid to a plurality of receptacles is in the field of immunology. Currently a number of different test procedures are being conducted using hetrogenous enzyme linked immuno absorbent assay techniques (Elisa). In this procedure, it is necessary to wash the receptacles with a wash solution to separate the bound components from the free components. Again, a tray containing ninety-six or more wells is commonly used.

This invention provides a simple, low cost and reliable device for adding a precise amount of liquid to a plurality of receptacles.

SUMMARY OF THE INVENTION

This invention is utilized to deliver liquid to receptacles defined in a tray having equally spaced wells or receptacles in columns and rows. For example, a typical titration tray has twelve rows and eight columns of receptacles, or vice versa. Such a tray is incrementally moved row by row under a plurality of dispensing orifices where liquid is dispensed to each receptacle or well of a row.

Briefly stated, the invention in one form thereof comprises a delivery system in which liquid is precisely dispensed to a plurality of aligned receptacles on a time-pressure basis. A closed container filled with the liquid to be dispensed is under a constant head of air pressure, greater than atmospheric. The container defines a liquid reservoir. This reservoir communicates with a common manifold which, in turn, supplies liquid to a plurality of equally spaced apart and aligned dispensing orifices in an orifice defining member. Disposed between the manifold defining member and the dispensing orifices in the orifice defining member are a plurality of parallel valve means in the form of flexible tubes which pass through a clamp. When the clamp is open, liquid flows through the plurality of parallel valve means to the orifices due to the head pressure in the reservoir. The orifices are aligned to coincide with the receptacles. With a constant head pressure, the amount of liquid dispensed is determined by the length of time the clamp is open.

A very sharp stop and start of the fluid flow is obtained by using a motorized cam to precisely open and close the clamp in a short but very closely controlled time period. By using a variable speed drive for the cam, the length of time the clamp is open may be varied. This determines the volume of liquid to be dispensed during such operation of the cam, and provides a precise means of calibrating the delivery volume equally to each of the receptacles.

Opening and closing of the clamp is in timed relation with an indexing drive that transports the tray and positions the rows of wells under the dispensing orifices.

The manifold and the orifice defining means are rigidly connected and the entire manifold assembly may be removed for easy autoclaving to achieve sterility.

The invention further utilizes a new and improved arrangement for achieving a constant air pressure. A movable weight is suspended in a closed tube by a column of air. This column of air is connected to the reservoir and make up air is supplied to the reservoir at a constant fixed pressure.

An object of this invention is to provide a new and improved apparatus for delivering precise amounts of liquid.

Another object of this invention is to provide an apparatus having new and improved means for precisely dispensing a predetermined quantity of liquid into a plurality of aligned wells.

The features of the invention which are believed to be novel are particularly pointed out and distinctly claimed in the concluding portion of this specification. The invention, however, both as to its operation and organization, together with further objects and advantages thereof, may best be appreciated by reference to the following detailed description taken in conjunction with the drawings.

BRIEF DESCRIPTION OF THE DRAWINGS

FIG. 2 is a view seen in the plane of lines 2—2 of FIG. 1;

FIG. 3 is a view seen in the plane of lines 3—3 of FIG. 2;

FIG. 4 is a view shown schematically as seen in the plane of lines 4—4 of FIG. 2;

FIG. 5 is a view seen in the plane of lines 5—5 of FIG. 2;

FIG. 6 is a sectional view of the manifold defining means seen in the plane of lines 6—6 of FIG. 1;

FIG. 7 is a view seen in the plane of lines 7—7 of FIG. 2 but with the warning mechanism rotated with respect to FIG. 2; and FIG. 8 is a plan view of a portion of a titration tray.

DETAILED DESCRIPTION OF THE ILLUSTRATED EMBODIMENT

Figure 1:
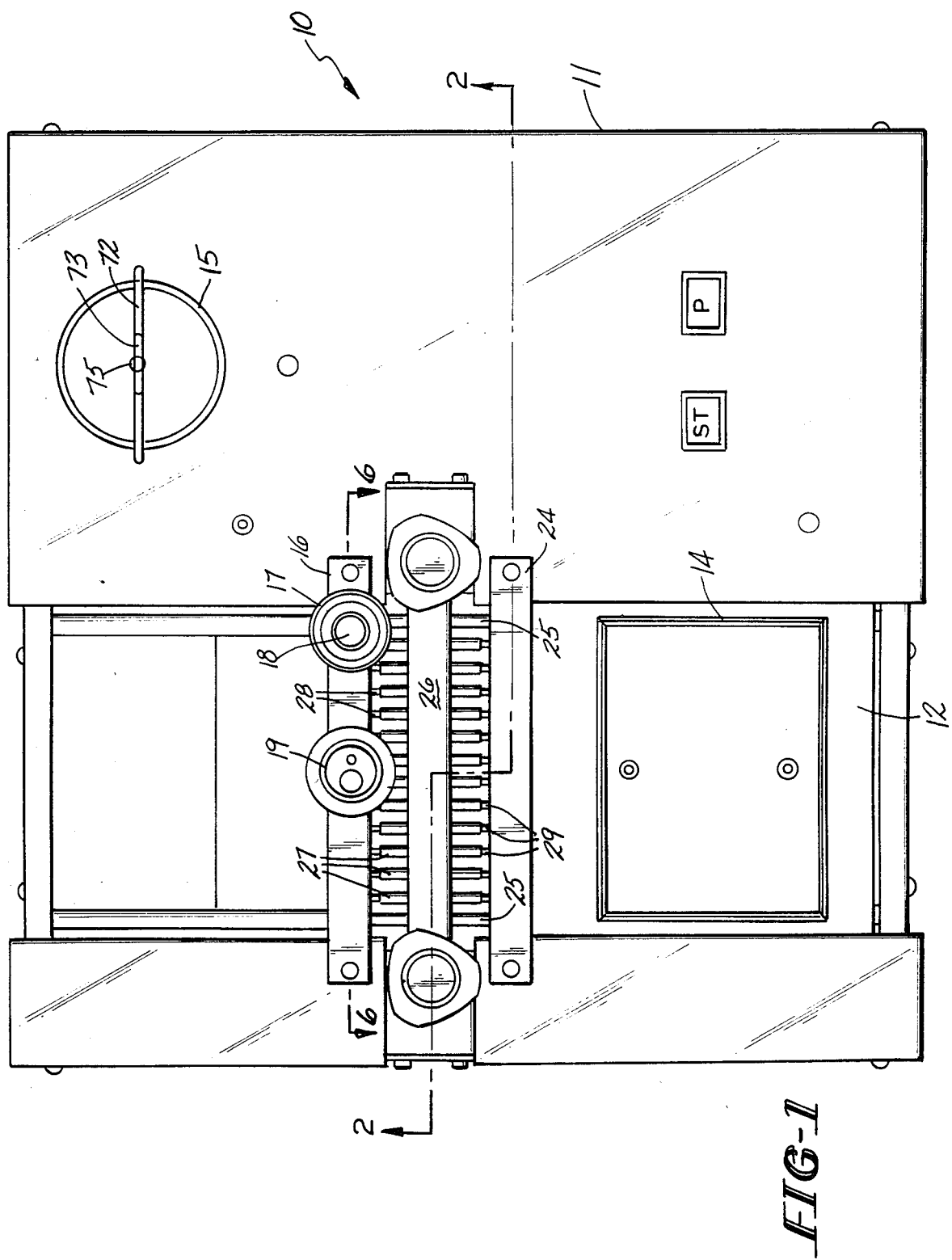
FIG. 1 is a top plan view of an apparatus embodying the invention.

Apparatus 10 embodying the invention as shown in FIG. 1 comprises a housing 11 defining a guideway for a tray platform 12 which moves beneath a liquid dispensing assembly 13. A tray locator 14 is defined on platform 12 to receive a tray T as partially shown in FIG. 8. A tubular member 15 which defines an air column extends upwardly from housing 11 for purposes hereinafter described.

The dispensing mechanism 13 comprises a first manifold defining member 16 having an air filter housing 17 thereon and an inlet port 18 adapted to be connected to a source of pressure above atmospheric. Also connected to manifold 16 is a receptacle 19 for receiving a bottle of liquid which defines a liquid reservoir.

Referring briefly to FIG. 6, manifold defining member 16 has defined therein a manifold 20 which communicates with a liquid reservoir providing bottle 21 through receptacle 19 and a passage 22. An air pressure line 23 provides communication from filter housing 17 to the reservoir.

With this arrangement, the pressure at the reservoir end of passage 23 is equal to the pressure due to the height of the fluid in the bottle plus the pressure of air in the reservoir above the fluid. This is the pressure in column 15.

Referring back to FIG. 1, manifold defining member 16 is rigidly connected to a second manifold in the form of an orifice defining member 24 by a pair of rods 25.

A stationary clamping member 26 is affixed to housing 11 as hereinafter described and extends longitudinally between orifice defining member 24 and manifold defining member 16. A plurality (twelve as shown) of resilient tubes 27 are connected between nipples 28 communicating with manifold 20 and nipples 29 extending from orifice defining member 24, each of which communicate with one of a plurality of twelve downwardly directed small pipes 30 received in passages 31 (FIG. 2) in member 24 as hereinafter described.

As shown in FIG. 3, a vertically movable clamping member 32 cooperates with fixed clamping member 26 to clamp or release clamping pressure on all of tubes 27. This arrangement provides in essence a valve between manifold 20 and the orifices in orifice defining member 24 which are simultaneously opened when clamping member 32 is lowered. At this time, the resilience of the tubes 27 causes them to spring open and a quantity of fluid will be delivered from manifold 20 to each of the orifices in member 24.

The manifold defining member 16 receives twelve (as shown) nipples 28 therein communicating with the manifold 20. These nipples are equally spaced to coincide with the input nipples 29 of orifice defining member 24.

A plurality of bores 31 are defined in orifice defining member 29, each receiving a pipe or tube 30 communicating with one of nipples 29. Orifice defining member 29 is cut-out about tubes 30 as indicated at 33 to decrease the effect of surface tension of liquid flowing through tubes 30.

Platform 12 moves on spaced apart guide rods 34 as shown in FIGS. 1 and 3. As shown in FIGS. 2 and 3, a drive shaft 35 has a spool 36 fast thereon wrapped with a wire 37. One end of wire 37 is secured in an adaptor 38 on one end of platform 12. The other end 39 of wire 37 is secured to a shaft 40 threadably received in an adaptor on the other end of platform 12.

A Geneva wheel 41 is affixed to shaft 35 (See FIG. 4) and defines four equiangularly positioned cam slots 42 and four equal arcuate surfaces 43. A pair of cams 44a and 44b are identically positioned on a cam drive shaft 47. Cam 44a carries thereon an eccentrically mounted indexing drive cam 45 (FIG. 4).

As cam 44a rotates, drive cam 45 once every rotation of cam 44a will engage a slot 42 and index Geneva wheel 41 ninety degrees. At the end of this ninety degree index, when drive cam 45 departs a slot 42, cams 44a and 44b will present flats 44c to cam followers 46 carried on vertically movable clamping member 32, thus permitting clamping member 30 to suddenly drop and permit the tubes 27 to open. As cams 44a and 44b continue to rotate, the circular portion of the periphery thereof will engage follower 46 and again raise follower 46 and cause lower clamping member 32 to quickly close tubes 27.

As shown in FIG. 2, there are two clamping cams 44a and 44b, one at either end of clamping member 32 and each acting on a follower 46 carried on clamping member 32. The cams 44a and 44b are fast on a drive shaft 47 which is connected through a gear box 48 to a variable speed motor 49 (See FIG. 2).

As shown in FIG. 4, a camming member 50 having an arcuate surface 51 designed to engage arcuate surfaces 43 of Geneva wheel 41 is carried on cam 44a to prevent any motion of Geneva wheel 41 except when driven by drive cam 45.

With this arrangement, platform 12 is indexed an incremental amount to sequentially present a row of wells W (FIG. 8) in a tray T precisely beneath the dispensing orifices defined by tubes 30 and then actuate the valving means by releasing clamp 32.

Reference is now made to FIG. 2. Upper or stationary clamping member 26 is affixed to housing 11 by means of fingernuts 53 secured to captured bolts 54. As shown on the lefthand side of FIG. 2, bolts 54 are captured by a nut 55.

A spring 56 disposed about each of bolts 54 reacts against an upper plate 57 and acts on clamp member 32 to move clamp member 32 downwardly if not held in the flow closure position by cams 44a and 44b. Thus, when clamping member 30 is released by cam 43, springs 56 will immediately move clamping member 30 downwardly. Springs 56 are enclosed in cavities 58 defined in plate member 57 and also in clamping member 32.

As shown in FIG. 2, column 15 receives therein a mass 59 having a seal 60 at the bottom thereof. Mass 59 is supported by a column of air and the weight of mass 59 thereon provides a constant pressure on the body of air in column 15. The bottom of column 15 which extends into housing 11 has a coupling 61 (FIG. 5) to the interior thereof and a line 62 leading to filter housing 17 (FIG. 2) through a quick disconnect coupling 63. The entire length of tubing 63 is not shown.

As shown in FIG. 5, platform 12 has side flanges 12a thereon adapted to actuate limit switches 66 and 67. Platform 12, as shown in FIGS. 2 and 3 has upstanding fingers 12b on either side thereof at the leading edge thereof, with respect to the position shown in FIG. 3. The purpose of the upstanding fingers 12b is to prevent opening of clamp member 32 until the first row of wells W in a tray T is beneath the dispensing orifices defined by tubes 30. Thus, the fingers 12b prevent dispensing of liquid until the platform 12 has moved to a position where the first row of wells of tray T is beneath the dispensing orifices.

Means are also provided to indicate when the supply of constant air pressure has been exhausted. Reference is made to FIGS. 2 and 7. A member 70 having a linear portion 71 is pivotally mounted in diametrical opposed cut-outs at the top of tube 15. Member 70 further comprises a semi-circular portion 72 having a preferably colored warning flag 73 at the top thereof. A flexible connector, such as a chain 74, extends from a cross member 75 in member 71 to a connection 76 to mass 59. When the mass 59 has moved down a sufficient distance, so that there is no longer a constant air pressure on manifold 20, it will tension chain 74 and rotate member 70 to an upright position as shown in FIG. 2, thus indicating that the constant source of air pressure has been exhausted. Tube 15 may be recharged by loosening the quick disconnect coupling 63 and lifting the mass upwardly, then replacing the quick disconnect coupling 63.

The amount of reagent delivered each dispensing cycle is controlled by the head pressure and the length of time the clamp or valve actuating member 32 is in an open position. In many cases, very small volumes, twenty-five to one hundred milliliters, are required on each delivery. To overcome the effects of service tension at the orifices, the flow must start and stop very quickly to provide an almost instantaneous change from the dynamic condition of flow to the static condition of restriction. If this rapid opening and closing is not attained, then the orifice will deliver liquid in drops rather than in a flowing stream. By providing variable speed motor driving cams 44a and 44b, the length of time the clamp is open can be adjusted. This provides a precise means of calibrating the delivery volume. The flat 44c on lifting cams 46 together with spring 56 provides very sharp start and stop of the fluid flow. The provision of the indexing drive through the delivery drive, that is, the drive cam together with the Geneva wheel indexing assures that the receptacles or wells W in a tray T are always correctly positioned under the delivery orifices each time the clamp 32 is opened for the liquid dispensing portion of the cycle. This relationship is not changed, even though the motor speed may be varied to adjust dispensing volume. The pressure at the manifold must be maintained constant. In the present invention, this is achieved by using the moving mass 59 in column 15. Since the weight of the mass and its area are fixed, the air column supporting the mass 59 remains at a constant pressure over the free travel range of the mass 59. Thus, make up air is supplied to the reagent container or reservoir 21 at a constant fixed pressure by a simple mechanical means.

The entire dispensing system 13 may be easily removed for autoclaving by removing the thumb nuts 53 and removing the manifold defining member and the orifice defining member which are rigidly connected together. The quick disconnect fitting may include a one-way valve.

When the air line 62 between the pressure column and the manifold 20 is disconnected, the operator may lift the weight to the top of its travel. Then, by inserting the air line 62 with its quick disconnect fitting 63 into coupling, the pressure column is connected to the reagent container in a closed system. When the air line is inserted into the quick disconnect coupling, it automatically opens a valve (not shown) into the coupling unit.

As replacement air flows into the liquid reservoir, the mass 59 falls in column 15 to compensate for the loss in volume while still maintaining a constant pressure head. Then, when the weight nears the bottom of its travel, the chain 74 causes the member 70 to rotate upwardly, displaying the warning flag 73 to the attendant. This serves as an alarm to advise that the constant air pressure is no longer being supplied to the system.

If desired, the air supply could be derived from any pressure regulated source, such as a self-contained, or separate air compressor, or from a replacable pressure bottle.

To operate the instruments, the operator places a tray T containing the receptacles or wells W to which the liquid is to be added on the tray holder 14 on platform 12. A cycle of operation is commenced by pressing power switch P initially and cycle start switch ST. Depressing the cycle start button ST (FIG. 1) causes the motor to run in the direction to advance the tray under the dispensing orifices. The tray table fingers 12b prevent opening of clamping member 30 and inhibit the addition of liquid to the wells of tray T until the first row of receptacles or wells of the tray is positioned under the dispensing orifices. On each index of platform 12, one-half of the desired volume is added to each row of receptacles. After the last row of receptacles has received the one-half desired volume, the forward flange 12a of platform 12 actuates rear limit switch 66 to cause the drive motor 52 to reverse. The tray table is now indexed in the reverse direction (to the left as viewed in FIG. 3). On each index, the remaining one-half of the liquid volume is delivered to each row of receptacles. After the last row has been filled, the tray table fingers 12b inhibit additional liquid dispensing to allow the tray to be indexed clear of the dispensing assembly for easy tray removal. When the tray platform 12 reaches the full forward position, it operates front limit switch 67 to stop the motor and resets the system for the next automatic cycle.

It may thus be seen that the objects of the invention set forth, as well as those made apparent in the foregoing description, are efficiently attained. While a preferred embodiment of the invention has been set forth for purposes of disclosure, modification to the disclosed embodiment of the invention, as well as other embodiments thereof, may occur to those skilled in the art. Accordingly, the appended claims are intended to cover all embodiments in the invention and modifications to the disclosed embodiment of the invention which do not depart from the spirit and scope of the invention.

What is claimed is:

1. A rehydrator for rehydrating material in spaced apart wells aligned in columns and rows in a titration tray, comprising means defining a plurality of spaced apart and aligned orifices, a tray platform movable beneath said orifice defining means between two reference positions so as to sequentially present a row of wells beneath said row of orifices, a liquid reservoir defining means coupled to said orifice defining means, means applying a constant pressure to said liquid in said reservoir, valve means connecting said reservoir defining means to said orifice defining means, valve actuating means, indexing means for incrementally indexing said platform, and drive means coupled to said indexing means and said valve actuating means to first index said platform a distance between the rows of wells of said tray and then to operate said valve actuating means to dispense a controlled volume of liquid under the constant pressure.

2. The rehydrator of claim 1 where said drive means includes a variable speed motor, and the amount of liquid dispensed into each well is determined by the speed of said motor.

3. The rehydrator of claim 1 further including a manifold defining means connected to said reservoir defining means, said manifold defining means providing a multiplicity of passages to said orifice defining means, a resilient tubing connecting each of said passages to an orifice, said valve actuating means including clamping means for pinching said tubes to prevent flow of liquid from said reservoir to said orifices and releasing said tubes to permit liquid to flow to said orifices.

4. The rehydrator of claim 1 wherein said valve means and said valve actuating means comprises a multiplicity of resilient tubes connecting said liquid reservoir to said orifices and a means for clamping and releasing said tubes to prevent passage of liquid to said orifices and permit passage of liquid to said orifices.

5. The rehydrator of claim 3 where said manifold defining means and said orifice defining means are rigidly connected.

6. The rehydrator of claim 5 wherein said manifold defining means includes a receptacle said reservoir defining means, and a passage is defined in said manifold defining means to said reservoir defining means to apply the constant pressure to liquid in said reservoir.

7. The rehydrator of claim 6 where said constant pressure supplying means comprises a tubular column, a mass in said column, and conduit means leading from the lower end of said column to said passage defined in said manifold defining means.

8. An apparatus for filling a multiplicity of receptacles each with a precise amount of liquid, comprising a manifold, a liquid reservoir coupled to said manifold, a multiplicity of tubes leading from said manifold to a like multiplicity of orifices where the orifices are to dispense liquid to receptacles therebelow, means providing a constant. Pressure on liquid in said reservoir, and time controlled valving means for opening and closing said tubes whereby the amount of liquid dispensed through each orifice is determined by the time said valving means opens said tubes.

9. The apparatus of claim 8 wherein said tubes are resilient and said valving means is a spring opened clamp, a cam driven by a variable speed motor for driving said cam, said cam periodically permitting opening of said clamp.

10. The apparatus of claim 9 where said wells are defined in rows and columns in a tray and said tray is indexed to present each row of wells beneath said orifices.

11. The apparatus of claim 10 further including a mechanism for indexing said tray, means on said cam for driving said indexing mechanism to position said tray beneath said orifices prior to said cam permitting opening of said clamp.

12. A device for dispensing a precise amount of liquid through each of a multiplicity of aligned orifices comprising means defining a first manifold, a means defining a closed liquid reservoir coupled to said first manifold, means for applying a constant fluid pressure to liquid in said reservoir defining means, a second manifold, said second manifold defining a plurality of aligned orifices, a plurality of resilient tubes connecting said first manifold to each of said orifices, clamping means disposed between said first and second manifolds adapted to clamp said tubes to prevent dispensing of fluid through said orifice defining means and to unclamp said tubes and permit dispensing of liquid through said orifices during the time said tubes are unclamped.

13. The device of claim 12 further including means for actuating said clamping means.

14. The device of claim 12 wherein said means for actuating includes means for varying the speed of said actuating means whereby the speed of said actuating means determines the amount of liquid dispensed.

15. The device of claim 12 adapted to dispense liquid to a plurality of aligned rows of wells in a tray where each row of wells of a tray is indexed beneath said orifices, said tray being positioned on an indexable platform, said clamping means is spring opened to permit dispensing of liquid through said tubes, camming means operative to cause said clamping means to close said tubes and periodically permit said clamping means to open, variable speed drive means for driving said camming means, indexing means, and means on said camming means for driving said indexing means to index said platform to present a row of wells beneath said orifices prior to said camming means permitting said clamping means to open.

16. The device of claim 12 where said means for applying constant pressure comprises a column having a mass therein supported on air and a conduit leading from the lower end of said column to said reservoir defining means.

17. The device of claim 16 further comprising means coupled to said mass for indicating that the pressure of air in said column is not constant.

18. The device of claim 12 where said first manifold is rigidly connected to said second manifold and said manifolds are removably mounted to said device.

19. The device of claim 11 wherein said indexing means is mounted to a shaft, a tray platform, a spool on said shaft, a cable wrapped about said spool and connected to opposite ends of said platform whereby when said indexing means drives said shaft, the indexing distance is determined by the spool diameter.

20. The device of claim 11 where said motor is reversible, one-half of the required liquid is dispensed to the wells during one direction of movement of said tray, and the other half of the required liquid is dispensed during the other direction of movement of the tray.

21. An apparatus for filling a multiplicity of receptacles each with a precise amount of liquid, comprising a manifold, a liquid reservoir coupled to said manifold, a member defining a multiplicity of orifices, a multiplicity of tubes leading from said manifold to a like multiplicity of orifices in said defining member where the orifices are to dispense liquid to receptacles therebelow, means spacing and rigidly connecting said manifold and said defining member, means providing a constant pressure on liquid in said reservoir, and time controlled valving means for opening and closing said tubes whereby the amount of liquid dispensed through each orifice is determined by the time said valving means opens said tubes.

22. The apparatus of claim 21 wherein said tubes are resilient and said valving means is a spring opened clamp, a cam driven by a variable speed motor for driving said cam, said cam periodically permitting opening of said clamp.

23. The apparatus of claim 21 where said wells are defined in rows and columns in a tray and said tray is indexed to present each row of wells beneath said orifices.

24. The apparatus of claim 23 further including a mechanism for indexing said tray, means on said cam for driving said indexing mechanism to position said tray beneath said orifices prior to said cam permitting opening of said clamp.

* * * * *

UNITED STATES PATENT AND TRADEMARK OFFICE
CERTIFICATE OF CORRECTION

PATENT NO. : 4,562,871
DATED : January 7, 1986
INVENTOR(S) : THOMAS A. ASTLE

It is certified that error appears in the above-identified patent and that said Letters Patent are hereby corrected as shown below:

IN THE CLAIMS

Claim 8, line 7, corresponding to Column 7, line 22:

After "constant" delete the period "." and change "Pressure" to --pressure--.

Signed and Sealed this

Twenty-seventh Day of May 1986

[SEAL]

Attest:

DONALD J. QUIGG

Attesting Officer

Commissioner of Patents and Trademarks